US 10,624,590 B2

(12) United States Patent
Brancaccio

(10) Patent No.: US 10,624,590 B2
(45) Date of Patent: Apr. 21, 2020

(54) DEVICE AND METHOD FOR ATTENTION AND FOCUS ACQUISITION AND MAINTENANCE

(71) Applicant: Richard Michael Brancaccio, Wake Forest, NC (US)

(72) Inventor: Richard Michael Brancaccio, Wake Forest, NC (US)

( * ) Notice: Subject to any disclaimer, the term of this patent is extended or adjusted under 35 U.S.C. 154(b) by 19 days.

(21) Appl. No.: 13/919,218

(22) Filed: Jun. 17, 2013

(65) Prior Publication Data

US 2014/0370471 A1    Dec. 18, 2014

(51) Int. Cl.
| | | |
|---|---|---|
| A61B 5/00 | (2006.01) | |
| A61B 5/16 | (2006.01) | |
| A61M 21/00 | (2006.01) | |
| A61B 5/053 | (2006.01) | |
| A61B 5/11 | (2006.01) | |

(52) U.S. Cl.
CPC ............ *A61B 5/7455* (2013.01); *A61B 5/168* (2013.01); *A61B 5/7405* (2013.01); *A61B 5/746* (2013.01); *A61M 21/00* (2013.01); *A61B 5/0533* (2013.01); *A61B 5/1118* (2013.01); *A61M 2021/0011* (2013.01); *A61M 2021/0022* (2013.01); *A61M 2021/0027* (2013.01); *A61M 2021/0044* (2013.01)

(58) Field of Classification Search
CPC ....... A61B 5/168; A61B 5/1118; A61B 5/746; A61B 5/0533; A61M 21/00; A61M 2021/0011; A61M 2021/0022; A61M 2021/0027; A61M 2021/0044

USPC ......................................................... 434/236
See application file for complete search history.

(56) References Cited

U.S. PATENT DOCUMENTS

| | | | |
|---|---|---|---|
| 5,402,108 A | 3/1995 | Tabin et al. | |
| 5,954,630 A | 9/1999 | Masaki et al. | |
| 6,461,316 B1 | 10/2002 | Lee et al. | |
| 6,558,165 B1 | 5/2003 | Curry | |
| 2004/0115603 A1 | 6/2004 | Reynolds | |
| 2007/0049788 A1* | 3/2007 | Kalinowski ............ | G09B 19/04 600/23 |
| 2007/0284401 A1* | 12/2007 | Hilliard ......................... | 222/638 |
| 2008/0288023 A1* | 11/2008 | John .................. | A61N 1/37247 607/59 |
| 2011/0128151 A1 | 6/2011 | Asad et al. | |
| 2012/0244503 A1 | 9/2012 | Neveldine | |
| 2013/0110895 A1 | 2/2013 | Valentino et al. | |

FOREIGN PATENT DOCUMENTS

| | | |
|---|---|---|
| CA | 2039671 A1 | 5/1991 |
| DE | 102010026781 A2 | 12/2012 |

OTHER PUBLICATIONS

Search Report and Written Opinion of the International Searching Authority, International application No. PCT/US2014/042630, dated Oct. 28, 2014.

* cited by examiner

*Primary Examiner* — Timothy A Musselman
(74) *Attorney, Agent, or Firm* — John L. Sotomayor

(57) ABSTRACT

The present invention relates to a device for focusing a user's attention for an individual who loses focus during an activity. This is accomplished by randomizing (which includes pseudo randomizing) each reminder prompts as well as the time interval within a selected time frame.

11 Claims, 2 Drawing Sheets

DEVICE AND METHOD FOR ATTENTION AND FOCUS ACQUISITION AND MAINTENANCE

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to attention focusing methods and devices. In particular it relates to a device which randomizes the stimulation pattern, the frequency of the stimulation pattern and the time interval of the stimulation in order for the individual to acquire and maintain focus.

Description of Related Art

Individuals with all sorts of conditions and situations suffer from difficulty in staying focused on a particular task for a given period of time. Conditions such as Attention Deficit Hyperactivity Disorder (ADHD) and autism spectrum disorders in their various iterations are developmental disorders in which focus and/or attention is difficult to maintain by an individual. Other disorders and injuries as well can leave an individual with great difficulty in staying focused on tasks. This is especially difficult for a student trying to maintain attention to a teacher in class, but is challenging for any situation where such an individual must pay attention to something for an extended period of time. Lack of attention in a school situation is especially difficult for children since lack of attention can lead to educational, behavioral and social difficulties as well as increased dropout rates in school. Adults likewise may have tremendous trouble staying focused on a particular task and may become defocused and lose concentration thus having trouble completing a given task. While the teacher or other leader in an attention based system might nudge a person back to attention or focus, frequently it is not recognized that a particular individual, student or the like is not paying attention. It is also difficult to constantly remind an individual and if there are multiple individuals in a task it may completely prevent completion of the task.

The art recognizes that an individual can be brought back to attention by constantly refocusing an individual and as the individual improves the intervals between reminders can be increased. A number of mechanical devices are known to be available for mechanical stimulation, however, it has also been found that many people become desensitized to the fixed stimulus or interval or both and the devices lose their effectiveness over time which is known as habituation. There is still a need for a device that can refocus an individual's attention to a task but not condition the individual to ignore the reminder.

BRIEF SUMMARY OF THE INVENTION

The present invention relates to the discovery that if the pattern of the attention prompting, the frequency vibrating signal (Stimulus Prompting Signal) and the interval of the timing of the stimulus prompting signal are varied randomly that the conditioning is avoided. Further, by limiting the random period of the time interval, the interval of the timed event can be lengthened or changed based on the individual needs for being refocused. Further, randomness in frequency can also improve/prevent habituation.

Accordingly, in one embodiment the present invention relates to an attention focusing device for supplying a plurality of attention prompting signals the device comprising:
   a) a circuit for producing a plurality of attention prompting signals, the circuit providing a random different attention prompting signal each time the prompting signal is supplied;
   b) a circuit for delivering the plurality of randomly produced attention prompting signals at a time when the user needs their attention focused.

In yet another embodiment, the present invention relates to a method of focusing a users attention for an individual who loses focus during an activity comprising:
   a) providing an attention focusing device for supplying a plurality of attention prompting signals to the user who has the device comprising:
      a circuit for producing a plurality of attention prompting signals, the circuit providing a random different attention prompting signal each time the prompting signal is supplied;
      a circuit for delivering the plurality of randomly produced attention prompting signals at a time when the user needs their attention focused;
   b) turning on the device when the activity begins;
   c) user loses focus;
   d) the device stimulates user into focus by providing a random attention prompting signal at a random time;
   e) repeating the attention prompting signal at the random interval until the activity is complete.

DETAILED DESCRIPTION OF THE INVENTION

Figure 1:
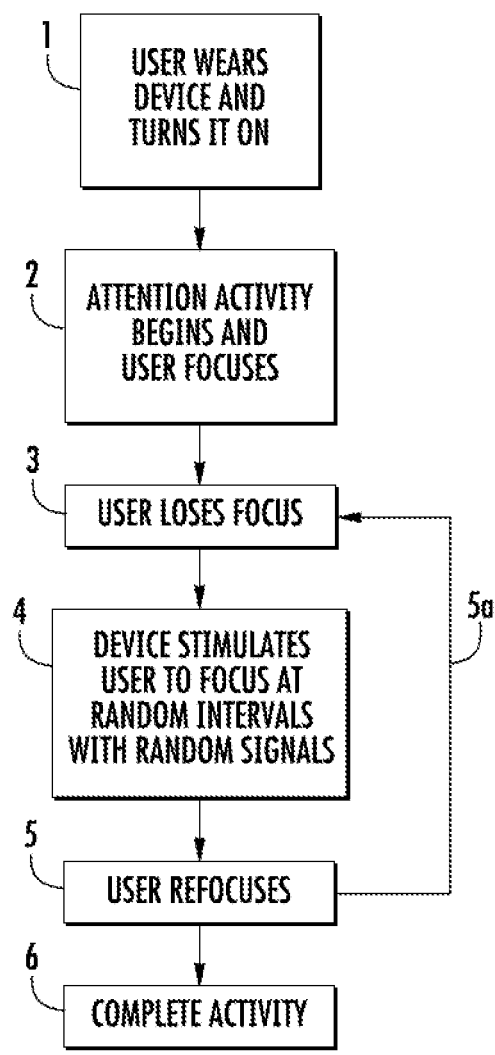
FIG. 1 is a flow chart of the method of the present invention.

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

Definitions

The terms "about" and "essentially" mean ±10 percent.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The term "comprising" is not intended to limit inventions to only claiming the present invention with such comprising language. Any invention using the term comprising could be separated into one or more claims using "consisting" or "consisting of" claim language and is so intended.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein an "attention focusing device" refers to an electronic device wired to produce an attention prompting signal of a particular random pattern at some random time interval and in one embodiment at random frequencies. Attention refers to either or both grabbing a user's attention and refocusing the individual user. The device can be a handheld device, a wrist mounted device, built into or added as an application to a smartphone, earpiece, or in general any device that the user can have close enough to receive the attention prompting signal. It can be a single device or be multiple devices coupled to operate together. Frequency is defined as the intensity, tone, length of tone or note intensity or the like.

As used herein an "attention prompting signal" refers to some signal that the user receives (hear, feel or see) to grab the user's attention (i.e. attention or focus) for a moment. The signal can be a sound, a tactile event or a visual signal such as a light. Sounds could be clicks, buzzes, tones, songs, or any type of sound that the user can hear. In one embodiment, the pattern of the sound remains the same but the frequency or tone is varied in the randomization of the signal. Tactile signals can be vibrations, tapping and the like and visual signals can be a light or a sign or the like that is visible to the user. These all have, in common, the ability to have some pattern to the attention prompting signal like a particular number of vibrations, series of blinks or a pattern to the taps or buzzes or the like or a combination of those which could be varied during the production of the prompting signal. In one embodiment, the pattern of the vibration may remain the same while the frequency or tone is varied in a random manner. Electronic circuits which can produce these types of signals are within the skill in the art in view of the present disclosure. The attention focusing device of the present invention is capable, once engaged, of producing the attention prompting signal a plurality of times such that the user is constantly brought back to attention and not just receive one reminder, or one type of reminder.

As used herein the phrase "random different attention prompting signal" refers to changing the attention prompting signal each time the attention prompting signal is delivered to the user such that the prompt does not necessarily repeat. This can be a limited bank of prompts or can truly be random or pseudo-random prompt. Typically, though, the attention prompting signal is relatively short in duration but that can be part of the randomization as well. So speed, frequency, pattern, and type can all be caused to change from attention prompting signal delivery to the attention prompting signal each time it is supplied.

As used herein the term "when the user needs their attention focused" refers to the delivery of the attention prompting signal to the user at a time when the user is likely to or is actually losing focus. So actual losing of focus can be measured by galvanic skin response, wide observation, movement, measurement and the like. Likely times can be for example, a set interval of times, adjustable intervals of time or a random time with a selected time range or the like.

As used herein, the term "when the user needs their attention focused" refers to the delivering the attention prompting signal to the user at a time when the user is likely to or is actually losing focus. So actual loss of focus can be measured by galvanic skin response, video observation, movement measurement and the like. Likely times can be adjustable interval of time for example, a set interval of time or a random time within a selected time range or the like.

As used herein the phrase "random time within a selected time range" refers to the delivery interval of the delivery of the attention prompting signal delivered by the device. In one sense, it is not meant to be entirely random since a time range must be selected to prevent virtually infinite ranges, and approximate how long a user can pay attention. So, for example, the range could be 5 to 10 minutes and the random time would be some interval within the selected range. The attention focusing device will have a circuit which can in one embodiment, be adjusted (either by the user or by someone else to prevent user adjustment of the interval) to change the time interval or range so that as a user gets better or worse the time interval range will be adjust to coincide with how long the user can pay attention before losing focus. So, for example, if the user with a 5 to 10 minute interval was improving the interval could be changed for example to 8 to 13 minutes or the like. The more the time interval can be varied in both length and start/stop time the more the device can be adjusted to suit the user. In one embodiment, there is a plurality of preprogrammed intervals and in other embodiments the intervals and or the start times can be set on the device. Randomness in the present invention can be accomplished by any convenient method. An algorithm, selected from a list, a pseudo-random pattern or the like can all be utilized. In one embodiment the random pattern is prevented from repeating or repeating consecutively.

In use, the attention focusing device would focus a user's attention for an individual user who loses focus or attention during an activity. As used herein an "activity" can be any event which the user must pay attention to. Examples include, but are not limited, to listening to a lecture, eating reminders, reduction of inappropriate or undesired affect behaviors and specific task completion such as, tests, exams, homework studies and the like.

The user arrives at the activity with the attention focusing device. The device as described above is then turned on as the activity commences. As the activity progresses the user will lose focus or attention or the like. The device will then stimulate the user into focusing on the activity by providing a random attention prompting signal at a time the user needs then attention focused as defined above. The device repeats the attention prompting signal for focusing the user until the activity has been completed.

Now referring to the drawings, FIG. 1 is a flow chart of the method of the present invention. In this embodiment, a user wears the device and turns it on 1. The activity that the user is to pay attention to begins 2. At some point in the activity the user loses focus. The time interval can be selected to coincide with the anticipated time the user will lose focus 3 or as described above. The device then stimulates the user which causes the user to focus and pay attention. The random interval, frequency and random signal being different or random each time 4. The user then refocuses 5 due to the reminder the signal gives the user. The user eventually defocuses again 5a and the process is repeated until the activity is complete 6.

Figure 2:
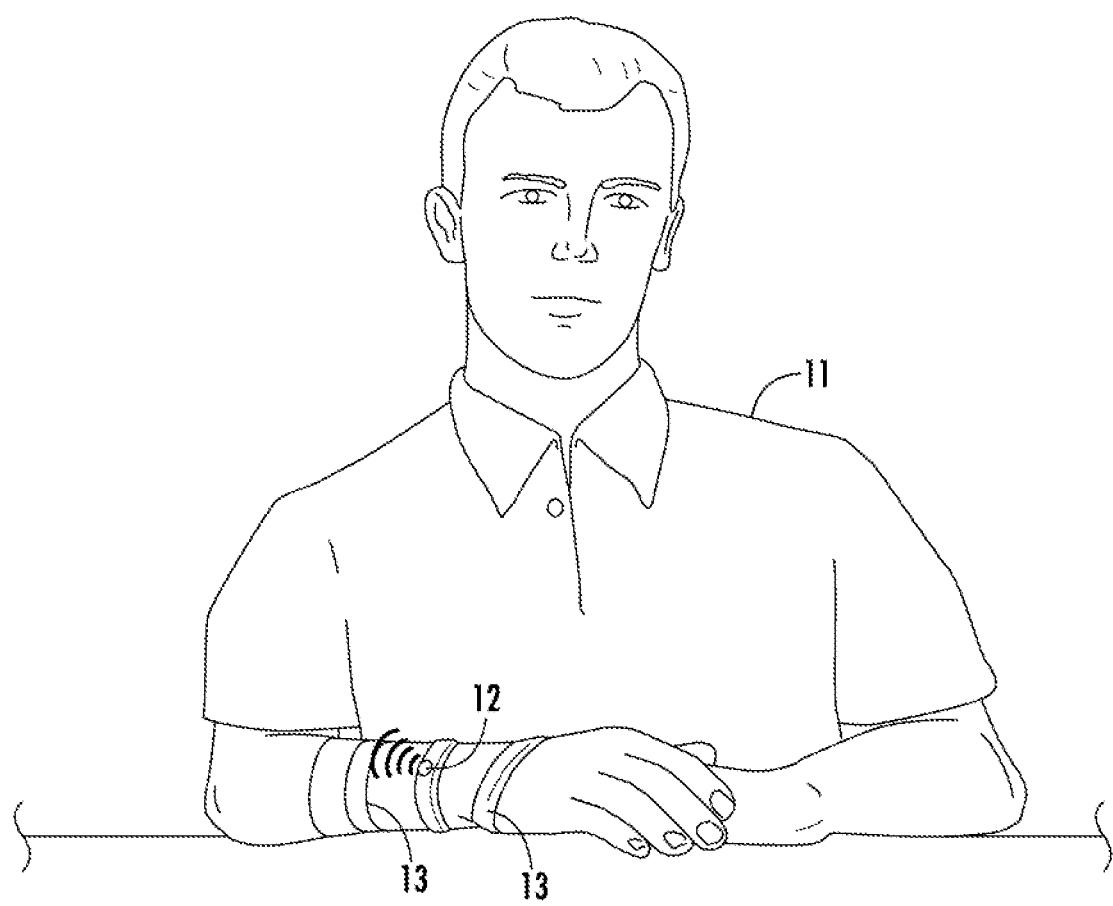
FIG. 2 is a device of the present invention on the user vibrating at a random time range.

FIG. 2 is a device of the present invention on the user vibrating at a particular or random time interval. In this view user 11 is wearing attention focusing device 12 as a wrist mounted device. The device vibrates 13 at a particular random pattern and at a time within a set time interval or range or by measuring the attention/focus of the user. The invention thus is that both the attention prompting signal and the time interval are randomized or at least pseudo randomized in order for the user not to become accustomed to the prompts given. Frequency could also optionally be varied randomly.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the applicant.

What is claimed is:

1. An attention focusing device for a user who needs to focus their attention comprising:
   a) a circuit for producing a plurality of attention prompting signals organized into a pattern, the circuit providing said pattern comprising a random different attention prompting signal each time the attention prompting signal is supplied;
   b) a circuit for establishing an adjustable time range;
   c) said circuit sending an attention prompting signal at random time intervals within said adjustable time range where each random time interval is shorter than said adjustable time range;
   d) a circuit for measuring the attention and/or focus of the user;
   e) a circuit for adjusting said adjustable time range to a different time range interval in response to loss of focus measurements indicating the attention focus of a user has changed;
   f) a circuit that repeatedly varies the pattern of the at least one randomly produced types of attention prompting signals that is delivered at random times by randomly varying the speed, frequency, and pattern contained within said attention prompting signal.

2. The attention focusing device according to claim 1 wherein the attention prompting signal is a sound, tactile or a visual signal.

3. The attention focusing device according to claim 1 which further comprises the attention prompting signal's randomly varying in frequency.

4. The attention focusing device according to claim 1 wherein there is a vibratory pattern.

5. The attention focusing device according to claim 1 wherein the time range can be adjusted.

6. A method of focusing a user's attention for an individual who loses focus during an activity comprising:
   providing an attention focusing device for supplying a plurality of attention prompting signals organized into a pattern to the individual;
   turning on the device when the activity begins;
   the device receiving an established adjustable time range;
   said device sending an attention prompting signal at random time intervals within said adjustable time range where each random time interval is shorter than said adjustable time range;
   the device measuring the attention and/or focus of the user;
   the device stimulating user into focus by providing a plurality of attention prompting signals organized into a pattern at a random time and transmitted to a user during said adjustable time range;
   the device adjusting said adjustable time range to a different time range in response to loss of focus measurements indicating the attention focus of a user has changed;
   repeating the providing of a plurality of attention prompting signals organized into said pattern at random intervals within said time range until the activity is complete.

7. The method according to claim 6 wherein the time range is lengthened as the user loses focus less frequently while participating in an activity.

8. The method according to claim 6 wherein the frequency of delivering said pattern is randomly varied.

9. The method according to claim 6 wherein the attention prompting signal includes a vibration with a different vibration pattern and time each time it is supplied.

10. The method according to claim 6 wherein the random times are derived from a value randomly selected from a research based data set.

11. The method according to claim 6 wherein the at least one of the randomly produced types of attention prompting signals is further randomized by randomly varying the intensity, length, or tone of at least one of the group consisting of speed and pattern.

* * * * *